United States Patent
Haverstick et al.

(10) Patent No.: US 7,180,076 B2
(45) Date of Patent: Feb. 20, 2007

(54) PHOTOIONIZATION DETECTORS, IONIZATION CHAMBERS FOR USE IN PHOTOIONIZATION DETECTORS, AND METHODS OF USE OF PHOTOIONIZATION DETECTORS

(75) Inventors: Jon K. Haverstick, Butler, PA (US); Daniel E. Bruce, Murrysville, PA (US); Michael B. Schulman, Pittsburgh, PA (US); Mark F. Zanella, Sr., Chicora, PA (US); James A. Cahall, Zelienople, PA (US); James B. Miller, Pittsburgh, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 11/093,992

(22) Filed: Mar. 30, 2005

(65) Prior Publication Data

US 2005/0218334 A1 Oct. 6, 2005

Related U.S. Application Data

(60) Provisional application No. 60/557,921, filed on Mar. 31, 2004.

(51) Int. Cl.
*B01D 59/44* (2006.01)
*A61N 5/00* (2006.01)

(52) U.S. Cl. .................. 250/382; 250/423 P; 250/372; 313/494; 313/324; 324/464

(58) Field of Classification Search ...................... None
See application file for complete search history.

(56) References Cited

U.S. PATENT DOCUMENTS 3,838,283 A 9/1974 Andersson 4,013,913 A 3/1977 Driscoll et al.

(Continued)

FOREIGN PATENT DOCUMENTS

EP 0 655 770 A 5/1995

(Continued)

OTHER PUBLICATIONS

RAE Systems. "Maintenance" Multirae Plus Operation and Maintenance Manual, [Online] Aug. 2002), pp. 4-1-4-3, XP002332053, Sunnyvale, CA, USA Retrieved from the Internet: URL:www.pksafety.com/pk_rae_multiraeplus_pgm50.pdf>, Figure 6.

(Continued)

*Primary Examiner*—Jack Berman
*Assistant Examiner*—Zia R. Hashmi
(74) *Attorney, Agent, or Firm*—James G. Uber; Henry E. Bartony, Jr.

(57) ABSTRACT

A photoionization detector includes a housing, electrical contacts within the housing and an easily removable and replaceable photoionization chamber within the housing. The photoionization chamber includes a cathodic electrode and an anodic electrode which may be coated with a thin layer of material. The photoionization chamber and the associated cathodic electrode and anodic electrode are removable from within the housing as a unit. The photoionization chamber makes electrical connection with the contacts when seated within the housing regardless of the orientation of the photoionization chamber about an axis.

20 Claims, 11 Drawing Sheets

U.S. PATENT DOCUMENTS

| | | | |
|---|---|---|---|
| 4,413,185 A * | 11/1983 | Leveson et al. | 250/423 P |
| 4,570,073 A | 2/1986 | Castleman | |
| 4,778,998 A | 10/1988 | Carnahan | |
| 5,338,931 A | 8/1994 | Spangler et al. | |
| 5,773,833 A | 6/1998 | Hsi et al. | |
| 6,313,638 B1 | 11/2001 | Sun et al. | |
| 2002/0036467 A1 | 3/2002 | Kawasaki | |
| 2004/0108857 A1* | 6/2004 | Jarski et al. | 324/464 |
| 2004/0168913 A1* | 9/2004 | Dean et al. | 204/431 |

FOREIGN PATENT DOCUMENTS

| | | |
|---|---|---|
| EP | 0 995 989 A | 4/2000 |
| EP | 0995989 | 4/2000 |
| FR | 2 546 627 A | 11/1984 |
| FR | 2546627 | 11/1984 |
| GB | 2 328 789 A | 3/1999 |
| GB | 2328789 | 3/1999 |
| GB | 2 345 134 A | 6/2000 |

OTHER PUBLICATIONS

RAE Systems:. "PID Sensor & Lamp Cleaning/Replacement", Minirae 2000 Operation and Maintenance Manual, [Online] Nov. 2001, pp. 7-4-7-6, XP002332054, Sunnyvale, CA, USA Retrieved from the Internet: URL:www.pksafety.com/pk_rae_minirae2000_pgm7600.pdf>.

Patent Abstracts of Japan, vol. 015, No. 392 (C-0873), Oct. 4, 1991 & JP 03 161010 A (Masahiro Morita), Jul. 11, 1991 abstract.

Patent Abstracts of Japan, vol. 2000, No. 09, Oct. 13, 2000 & JP 2000 182569 A (Matsushita Electric Works LTD), Jun. 30, 2000 abstract.

Patent Abstracts of Japan, vol. 01996 No. 05, May 31, 1996 & JP 08 005789 A (Toshiba Corp), Jan. 12, 1996, the whole document.

RAE Systems: "Maintenance" Multirae Plus Operation and Maintenance Manual, 'Online! Aug. 2002), pp. 4-1 to 4-3, XP002332053, Sunnyvale, CA, USA: Retrieved from the Internet: URL:www.pksafety.com/pk_rae_multiraeplus_pgm50.pdf>, 'retrieved on Jun. 15, 2005! figure 6.

Rae Systems: "PID Sensor & Lamp Cleaning/Replacement" Minirae 2000 Operation and Maintenance Manual, 'Online! Nov. 2001, pp. 7-4 to 7.6, XP002332054, Sunnyvale, CA USA: Retrieved from the Internet: URL: www.pksafety.com/pk_rae_minirae2000_pgm7600.pdf> 'retrieved on Jun. 15, 2005! figure 7.2.

* cited by examiner

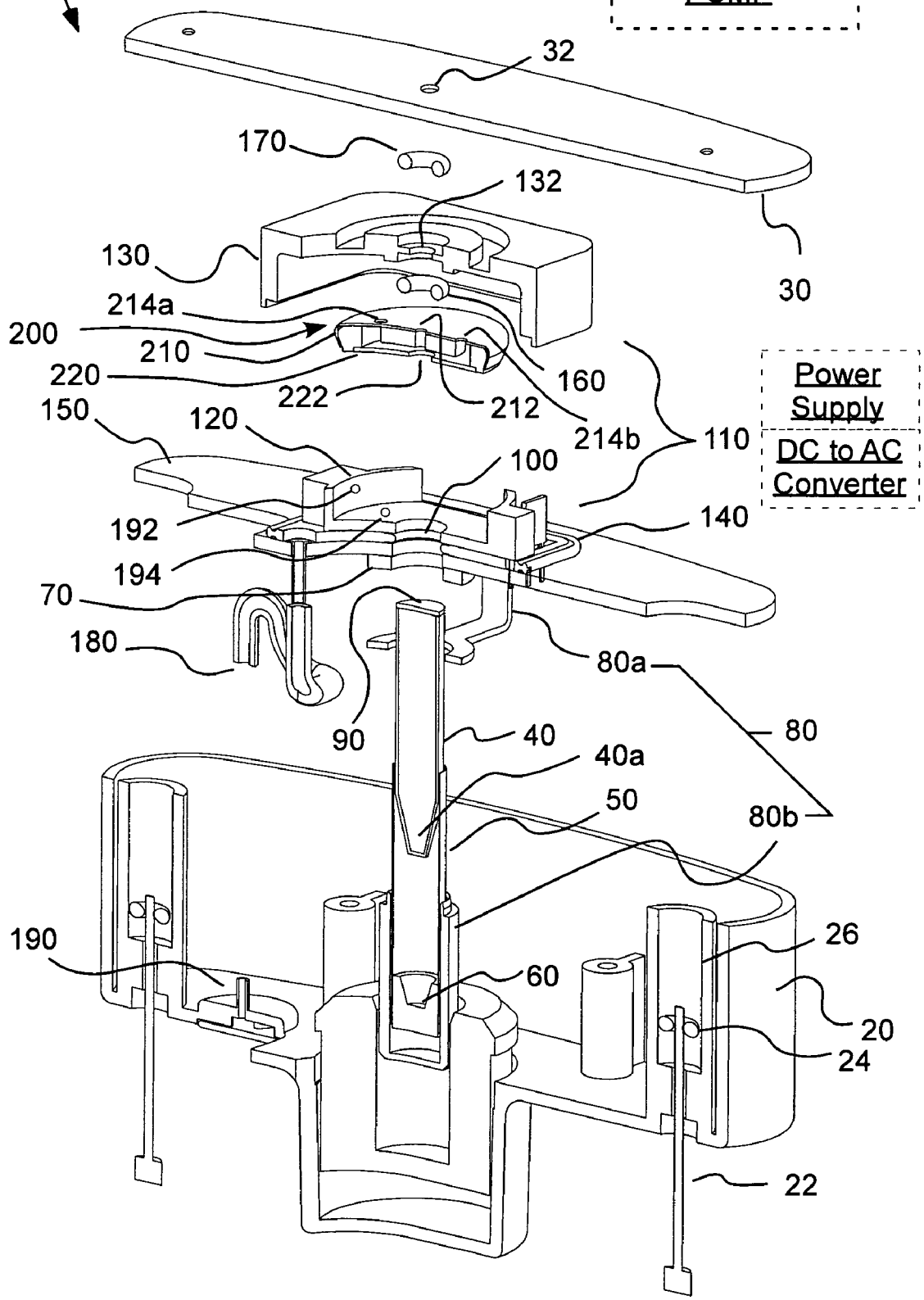

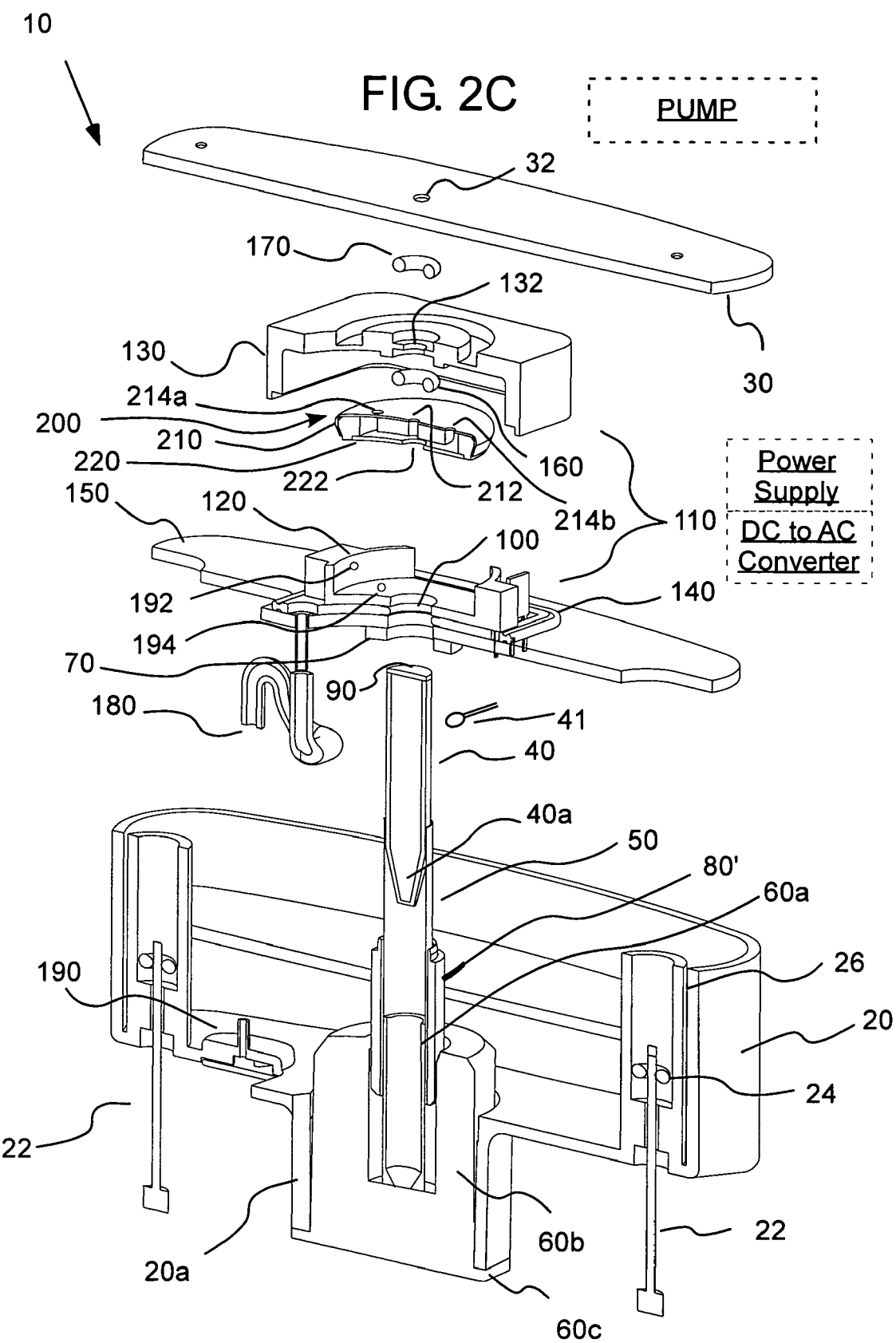

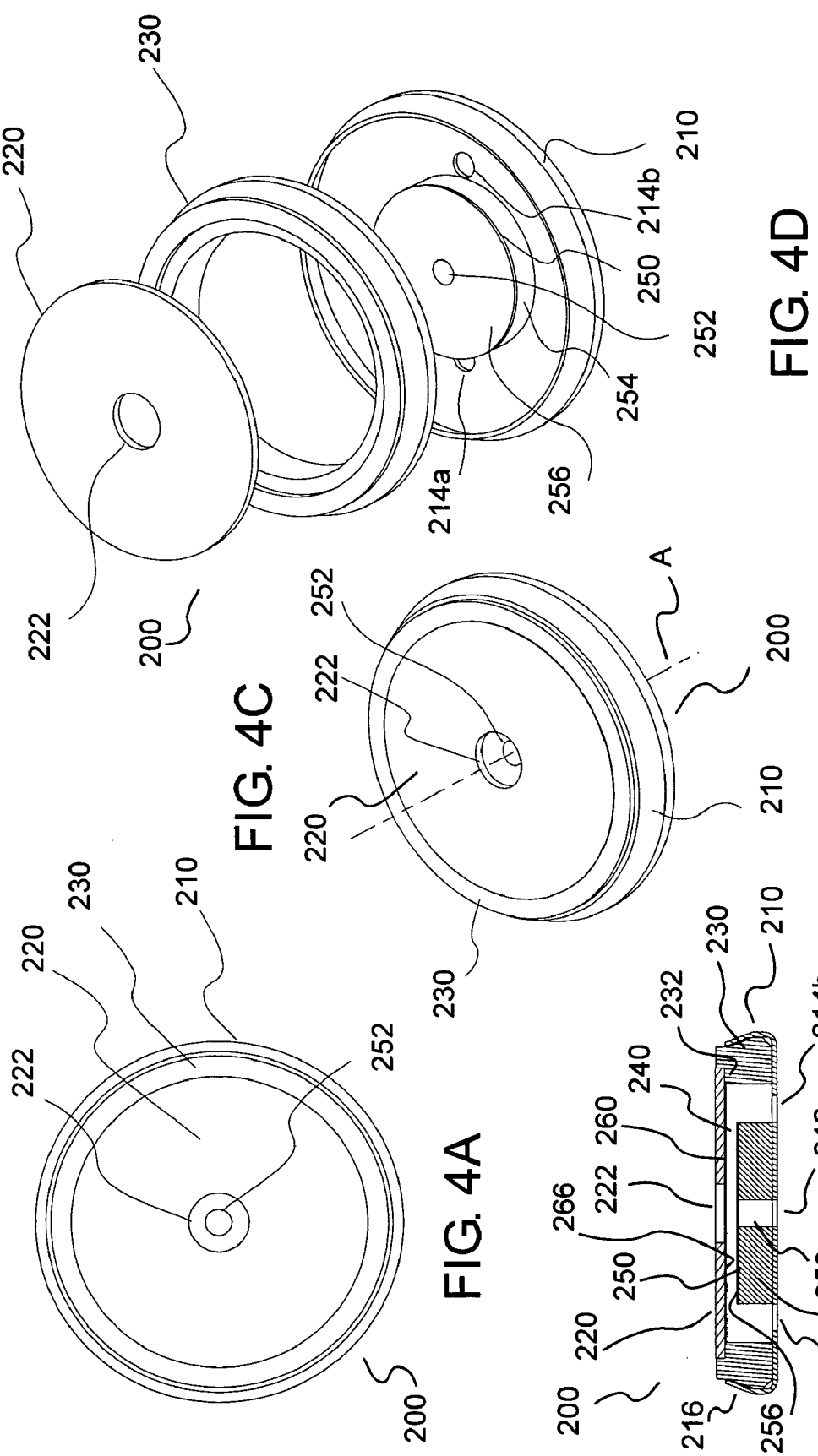

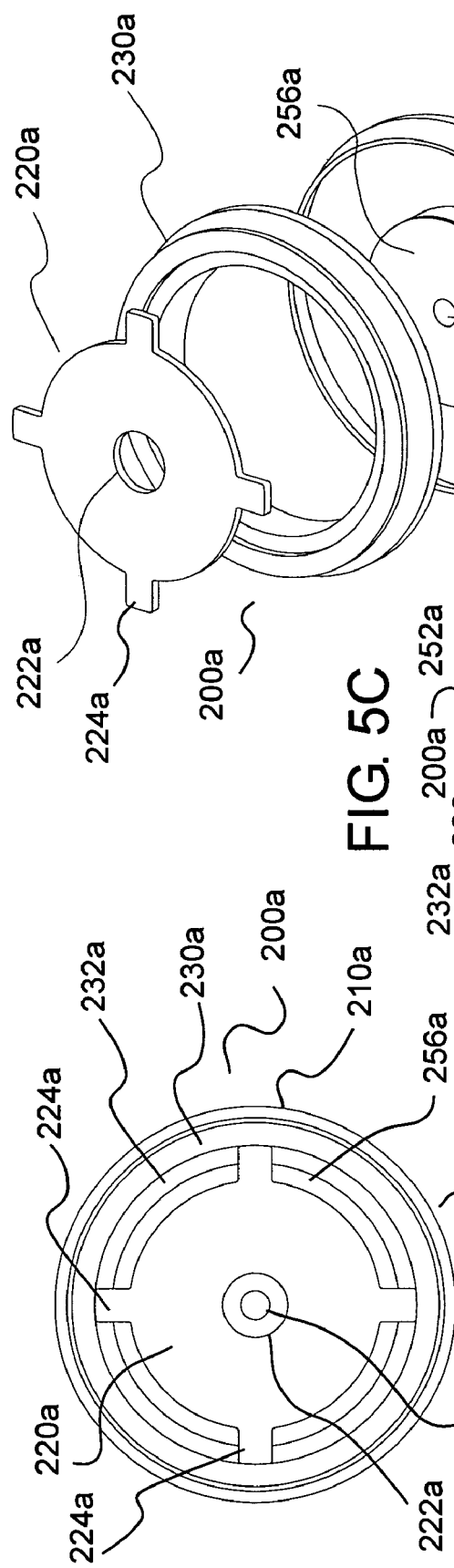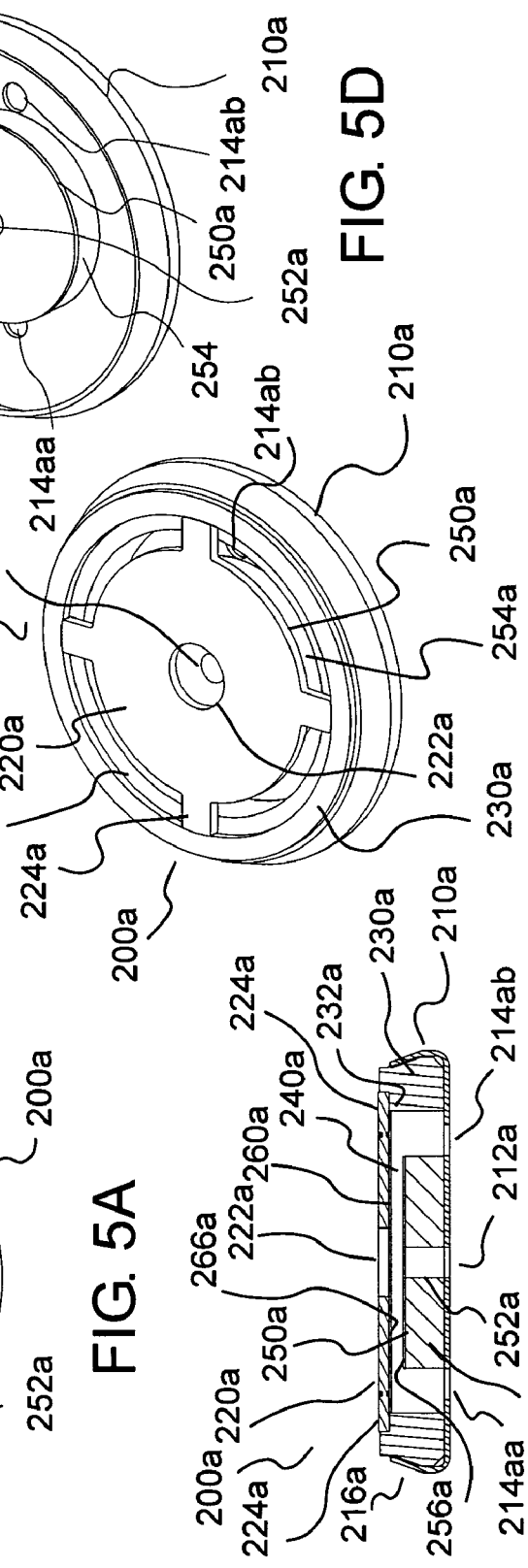

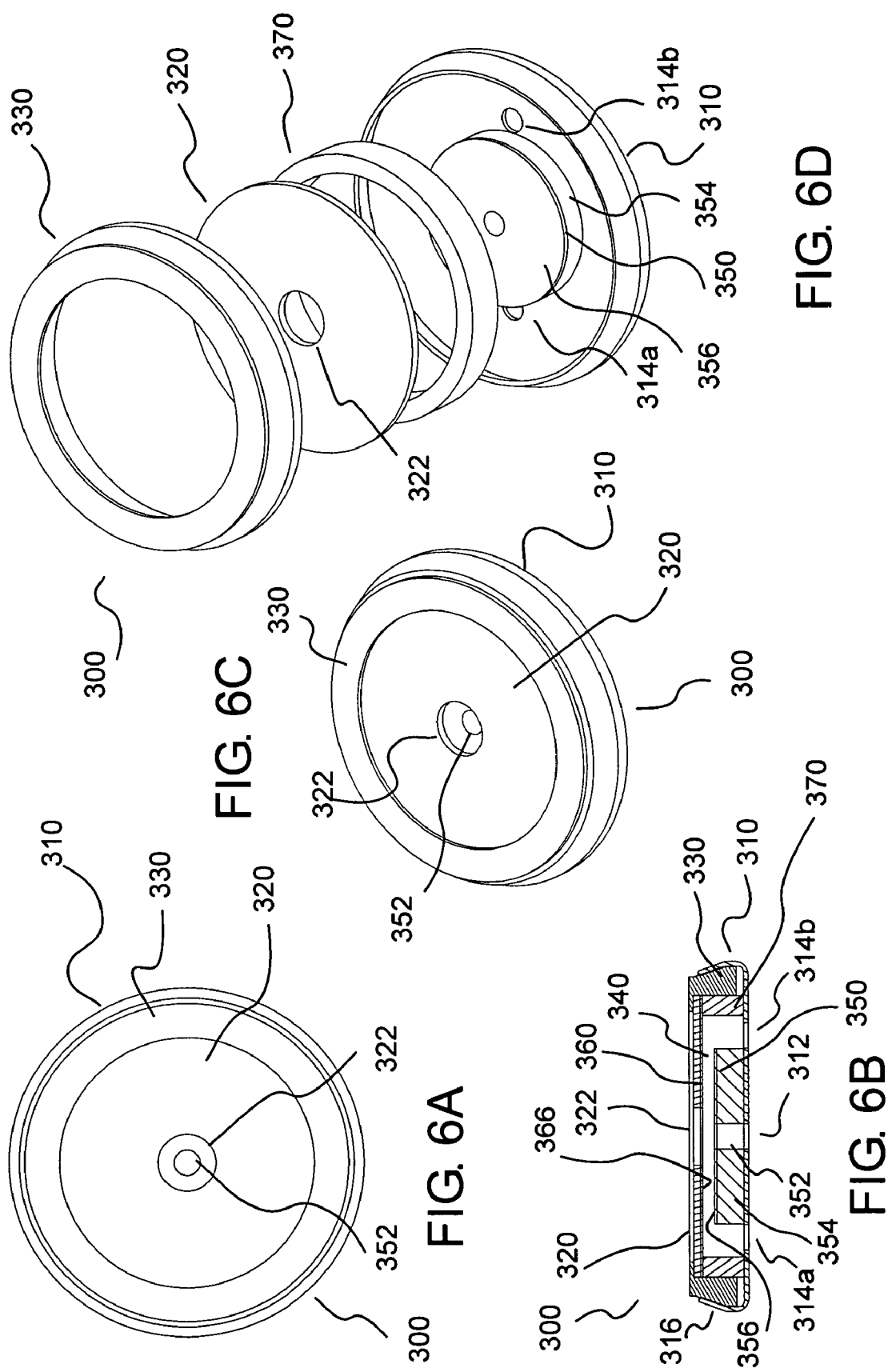

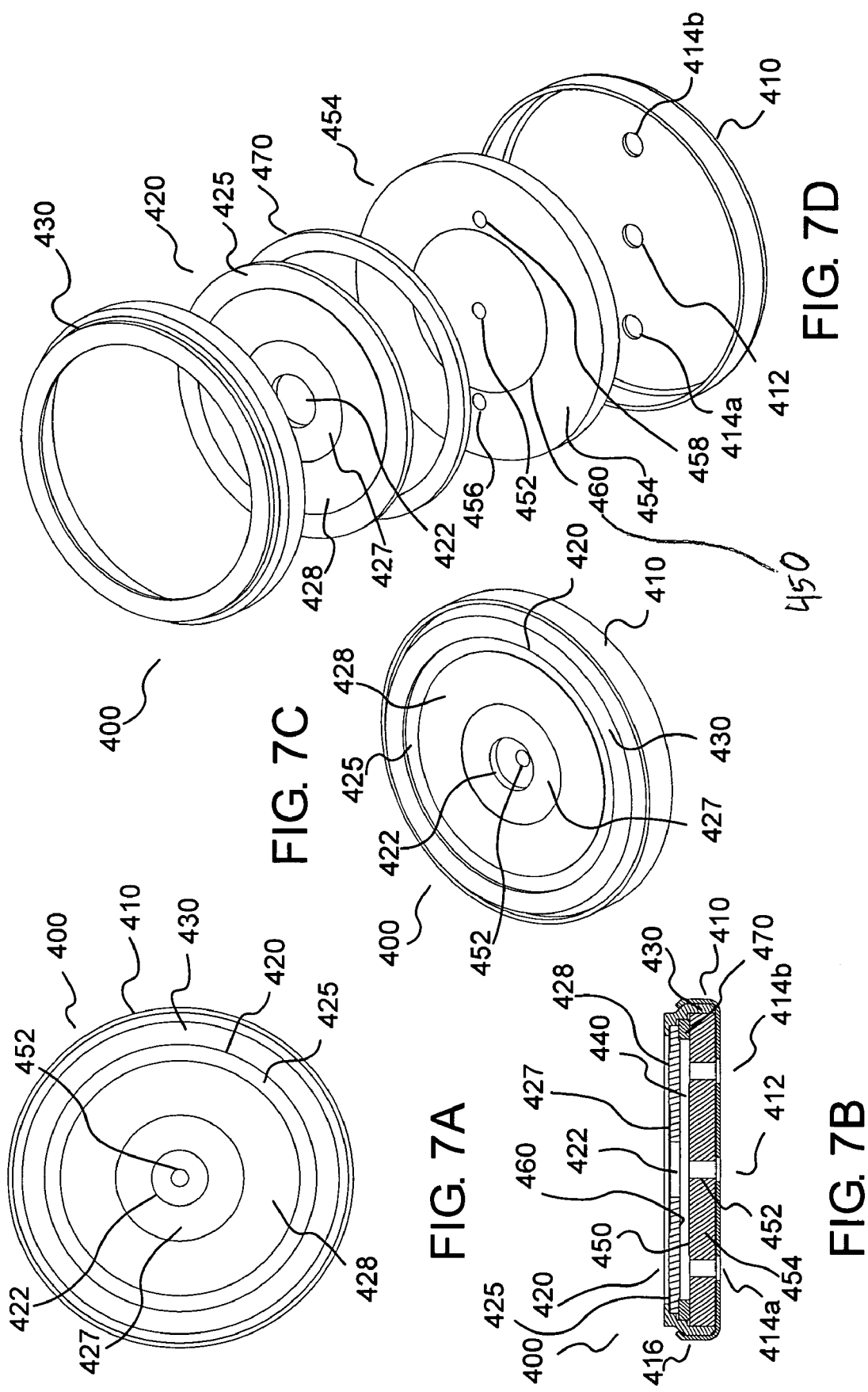

PHOTOIONIZATION DETECTORS, IONIZATION CHAMBERS FOR USE IN PHOTOIONIZATION DETECTORS, AND METHODS OF USE OF PHOTOIONIZATION DETECTORS

CROSS-REFERENCE TO RELATED APPLICATION

This application claims the benefit of U.S. Provisional patent application No. 60/557,921 filed Mar. 31, 2004, the disclosure of which is incorporated herein by reference.

BACKGROUND OF THE INVENTION

The present invention relates generally to photoionization detectors, to ionization chambers for use in photoionization detectors, and to methods of use of photoionization detectors.

Several photoionization detectors are described, for example, in U.S. Pat. Nos. 4,013,913; 4,398,152; 5,561,344; 6,225,633 and 6,646,444; and in German Patent DE 19535216 C1. In a typical photoionization detector (PID), a miniature gas-discharge lamp is used to produce high-energy vacuum ultraviolet (VUV) photons. In one approach, a large high-frequency voltage is applied between electrodes which are adjacent to the lamp bulb in order to induce an ionization, excitation and photoemission process in the gas which is sealed within the lamp bulb. Some of the resulting VUV photons pass through a VUV-transmissive window in the lamp to illuminate an adjacent volume within an electrically-biased ionization chamber, into which a sample of gas is introduced. Depending on the ionization potentials of the various species in the sampled gas and the maximum photon energy of the VUV radiation, photoionization of some of the gas molecules introduced into the ionization chamber can thus occur and be detected. An electrodeless (that is, having no internal electrodes), miniature PID gas discharge lamp is described, for example, in U.S. Pat. No. 5,773,833.

Typically the ionization chamber of a PID is constructed with a housing formed integrally within the PID sensor, and at least one pair of closely-spaced electrodes is positioned within the ionization chamber. The gas to be analyzed is introduced into the chamber through at least one gas inlet and leaves the chamber through at least one gas outlet. The window of the lamp is positioned so as to illuminate the sampled gas molecules with VUV photons as they move toward or within the volume between the ionization chamber electrodes. A voltage applied between these electrodes generates a high electric field across their gap, which forces the ions and electrons resulting from the photoionization process to move toward the lower or higher potential electrode, respectively. Usually an electrometer circuit is used to measure the ion current flowing to the cathode electrode. The presence of photo-ionizable molecules in the sampled gas is thereby detected. The sensitivity of a particular PID design to a variety of ionizable compounds can be determined relative to its calibrated sensitivity to a standard compound. The use of a hand-held PID device to detect trace levels of volatile organic compounds (VOCs) is one particularly important application of this technique.

It is well known that the presence of water vapor in the gas flow (as quantified by the relative humidity) can alter the sensitivity and the background signal level of a PID. Various techniques have been developed to reduce or correct for this effect. For instance, U.S. Pat. No. 4,778,998, assigned to Mine Safety Appliances Company, describes a PID in which a humidity sensor, a temperature sensor and a microcomputer (microprocessor) are used to apply a predetermined correction factor to compensate for the cross-sensitivity of the PID to the relative humidity.

As a PID lamp is operated with its window exposed to trace hydrocarbon and organo-silicone compounds in a sample of ambient air, the window surface tends to become increasingly contaminated by a surface film which is formed from the photoionization products of these air-borne compounds. This causes the effective lamp output intensity to decrease slowly with operating time. The typical maintenance procedure for PID instruments thus requires removal of the lamp and cleaning of the window manually when the sensitivity has dropped below a certain level.

Current types of PID instruments have several substantial disadvantages. For example, U.S. Pat. Nos. 5,773,833 and 6,225,633 disclose multilayer ionization chambers for a PID which are fabricated from multiple layers of machined PTFE and stainless steel, making the ionization chambers relatively difficult and expensive to manufacture. In those designs, the multilayer ionization chambers are held together by metallic pins. The metallic pins also function as electrical contacts for the ionization chamber and removably attach the sensor ionization chamber to the remainder of the instrument. Ionization chambers similar to those described in U.S. Pat. Nos. 5,773,833 and 6,225,633 are found for example in the TOXIRAE PLUS and MULTIRAE PLUS instruments available from RAE Systems, Inc. of Sunnyvale, Calif.

Furthermore, with extended operating time the electrodes within the ionization chamber become contaminated by the process described above, resulting in leakage currents and inaccurate measurements. It is quite difficult and relatively expensive to repair or restore an ionization chamber by opening it and removing this contamination. For example, as described in the Operation Manual for the TOXIRAE PLUS sensor, its sensor ionization chamber can be gently removed from the instrument for cleaning, and the ionization chamber is to be cleaned in a methanol bath (an ultrasound bath is highly recommended). After cleaning, the sensor ionization chamber can be reattached to the remainder of the instrument. Precise alignment of the sensor ionization chamber with dedicated pin contact seatings in the remainder of the instrument is required for reattachment of the TOXIRAE PLUS and MULTIRAE PLUS sensor ionization chambers.

As an alternative to manual cleaning, an enhanced concentration of ozone is purported to loosen or remove organic deposits from these surfaces to some degree. Schemes for self-cleaning the ionization chamber and the VUV lamp window, which rely on operating the VUV lamp during exposure to an oxygen-containing atmosphere in order to generate ozone, have been described. See for example U.S. Pat. No. 6,313,638. However, these self-cleaning schemes also present disadvantages, which are discussed below.

Depending on the minimum wavelength that must be transmitted, only a small number of crystalline materials, such as $CaF_2$, $BaF_2$, $MgF_2$ or LiF, are usable as VUV windows for PID lamps. The transmission of these VUV window materials reduces sharply below about 140 nm. The shortest wavelength transmission is provided by LiF optical material, but the transmission of LiF is degraded over time by color-center formation ("solarization") in the crystal due to exposure to the VUV radiation. Indeed, product specifications for a miniature LiF-window PID gas-discharge lamp which is available from RAE Systems, Inc., of Sunnyvale, Calif., indicate that the lamp is limited to an operating life of less than several hundred hours.

An alternative method is described in U.S. Pat. No. 6,255,633 for producing a self-cleaning action on the VUV lamp window and on the internal surfaces of the ionization chamber in a PID device. This requires stopping the gas flow in the ionization chamber and operating the VUV lamp to produce a higher concentration of ozone in the static sample. However, for a lamp with a LiF window this method exacerbates degradation of the LiF material due to color-center formation by the VUV radiation, and the repeated self-cleaning cycles will use up a significant fraction of its limited available operating life. This reduction of the useful operating life applies to a lesser extent to any type of VUV lamp which is self-cleaned by methods similar to that of U.S. Pat. No. 6,255,633.

For the above reasons it is therefore desirable to develop improved photoionization detectors, ionization chambers for use in photoionization detectors, and methods of use and assembly of photoionization detectors.

SUMMARY OF THE INVENTION

In one aspect, the present invention provides a photoionization detector including a housing, electrical contacts within the housing and a photoionization chamber within the housing. The photoionization chamber includes a cathodic electrode and an anodic electrode. The photoionization chamber and the associated cathodic electrode and anodic electrode are removable from within the housing as a unit. The photoionization chamber makes electrical connection with the contacts when in the housing regardless of the orientation of the photoionization chamber about its axis. The photoionization detector also preferably includes a lamp to transmit VUV energy to within the photoionization chamber.

In one embodiment, a side of the cathodic electrode which attracts positively charged reaction products is coated with a layer of a nonconductive material. The layer of nonconductive material allows the detection of at least a portion of the positively charged reaction products impinging upon the layer. The layer of non-conductive material on the cathodic electrode can also be VUV absorptive. A side of the anodic electrode which repels positively charged reaction products can also or alternatively be coated with a layer of nonconductive material. Once again, the layer of material on the anodic electrode can also be VUV absorptive. Preferably, such layers of material on the cathodic electrode and/or anodic electrode are of generally uniform thickness over the coated area of the electrode.

In a further embodiment, the photoionization chamber housing includes a first housing member in electrical connection with the cathodic electrode. At least a portion of the surface of the first housing member forms a first electrical contact. The housing further includes a second housing member in electrical connection with the anodic electrode. At least a portion of the surface of the second housing member forms a second electrical contact. The first housing member can be formed entirely from a conductive metal. Likewise, the second housing member can be formed entirely from a conductive metal. The first housing member and the second housing member can, for example, be mechanically connected to an insulating connector. Such a connector can be annular in shape. In one embodiment, the first housing member and the second housing member are mechanically connected to an annular, insulating connector via crimping.

In another aspect, the present invention provides a photoionization chamber for use within a housing of a detector including a cathodic electrode and an anodic electrode spaced from the cathodic electrode. The photoionization chamber also includes a first housing member, wherein at least a portion of the surface of the first housing member forms a first electrical contact in electrical connection with the cathodic electrode. The photoionization chamber further includes a second housing member, wherein at least a portion of the surface of the second housing member forms a second electrical contact in electrical connection with the anodic electrode. The second electrical contact is electrically insulated from the first electrical contact. The photoionization chamber is removable from the housing of the detector.

The first housing member and the second housing member can be mechanically connected to a single connector. The first housing member can be formed from a conductive metal. Similarly, the second housing member can be formed from a conductive metal. As discussed above, the first housing member and the second housing member can be mechanically connected to an annular, insulating connector (via, for example, crimping).

In a further aspect, the present invention provides a photoionization detector including a housing and a photoionization chamber within the housing. The photoionization detector also includes a first housing member and a second housing member. The first housing member and the second housing member are mechanically connected to a single, electrically insulating connector. The photoionization chamber further includes a cathodic electrode in electrical contact with the first housing member and an anodic electrode in electrical contact with the second housing member. The photoionization chamber and the included cathodic electrode and anodic electrode are removable from within the detector housing as a unit. The photoionization detector also preferably includes a lamp to transmit VUV energy into the photoionization chamber.

In another aspect, the present invention provides a photoionization chamber including a cathodic electrode and an anodic electrode. The cathodic electrode includes a layer of a nonconductive material coated upon a side of the cathodic electrode which attracts positively charged reaction products. The layer allows the detection of at least a portion of positively charged reaction products impinging upon the layer. The anodic electrode includes a layer of a nonconductive material coated on a side of the anodic electrode which repels positively charged photoionization reaction products into a volume between the cathodic electrode and the anodic electrode.

The present invention utilizes a VUV lamp including an enclosure containing a discharge gas or gas mixture. One or more portions of the enclosure include a VUV transmissive section of crystalline material to transmit VUV radiation. A portion of the enclosure can be fabricated from another material to which the crystalline VUV transmissive section(s) can be hermetically sealed. For example, the material can be glass, ceramic or quartz.

In still a further aspect, the present invention provides a photoionization detector including a housing, a photoionization chamber within the housing, and a VUV lamp to transmit VUV energy to within the photoionization chamber. The photoionization detector further includes at least one restrictive orifice in the gas flow path into the ionization chamber, such that a pressure on the photoionization chamber side of the orifice is less than the pressure on the other (inlet or ambient) side of the orifice. The restrictive orifice(s) reduce the relative humidity of sample gas within the photoionization chamber as compared to the relative humidity in the ambient environment, thereby making the photoionization chamber less sensitive to ambient relative humidity. In one embodiment, a single restrictive orifice is placed in the gas flow path. In another embodiment, a plurality of restrictive orifices are placed in the gas flow path. The plurality of restrictive flow paths can, for example, be formed in a filter (for example a porous frit) having a correspondingly small pore diameter.

BRIEF DESCRIPTION OF THE DRAWINGS

FIG. 1 illustrates a cutaway, perspective, exploded or disassembled view of an embodiment of a PID of the present invention.

FIG. 2C illustrates a cutaway, perspective, exploded or disassembled view the PID of FIG. 1 including an alternative electrode configuration.

FIG. 4A illustrates a top plan view of an embodiment of an ionization chamber of the present invention.

FIG. 4B illustrates a side, cross-sectional view of the ionization chamber of FIG. 4A.

FIG. 4C illustrates a perspective view of the ionization chamber of FIG. 4A.

FIG. 4D illustrates a perspective, exploded view of the ionization chamber of FIG. 4A.

FIG. 5A illustrates a top plan view of another embodiment of an ionization chamber of the present invention.

FIG. 5B illustrates a side, cross-sectional view of the ionization chamber of FIG. 5A.

FIG. 5C illustrates a perspective view of the ionization chamber of FIG. 5A.

FIG. 5D illustrates a perspective, exploded view of the ionization chamber of FIG. 5A.

FIG. 6A illustrates a top plan view of another embodiment of an ionization chamber of the present invention.

FIG. 6B illustrates a side, cross-sectional view of the ionization chamber of FIG. 6A.

FIG. 6C illustrates a perspective view of the ionization chamber of FIG. 6A.

FIG. 6D illustrates a perspective, exploded view of the ionization chamber of FIG. 6A.

FIG. 7A illustrates a top plan view of another embodiment of an ionization chamber of the present invention.

FIG. 7B illustrates a side, cross-sectional view of the ionization chamber of FIG. 7A.

FIG. 7C illustrates a perspective view of the ionization chamber of FIG. 7A.

FIG. 7D illustrates a perspective, exploded view of the ionization chamber of FIG. 7A.

DETAILED DESCRIPTION OF THE INVENTION

Figure 2A:
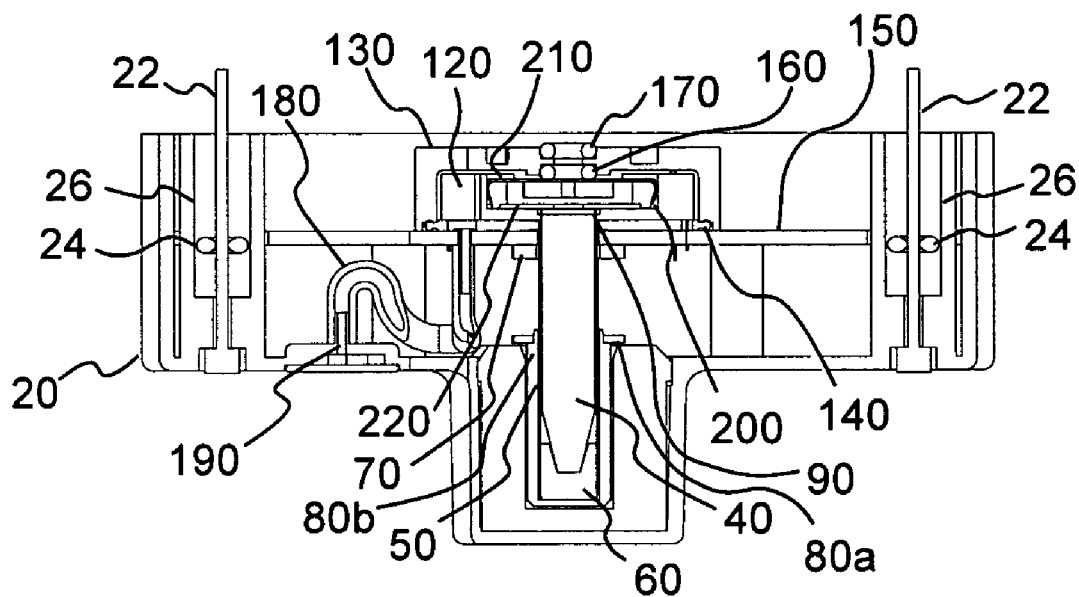
FIG. 2A illustrates a cutaway, side view of the PID of FIG. 1 in an assembled state, other than the top enclosure or cap.
Figure 2B:
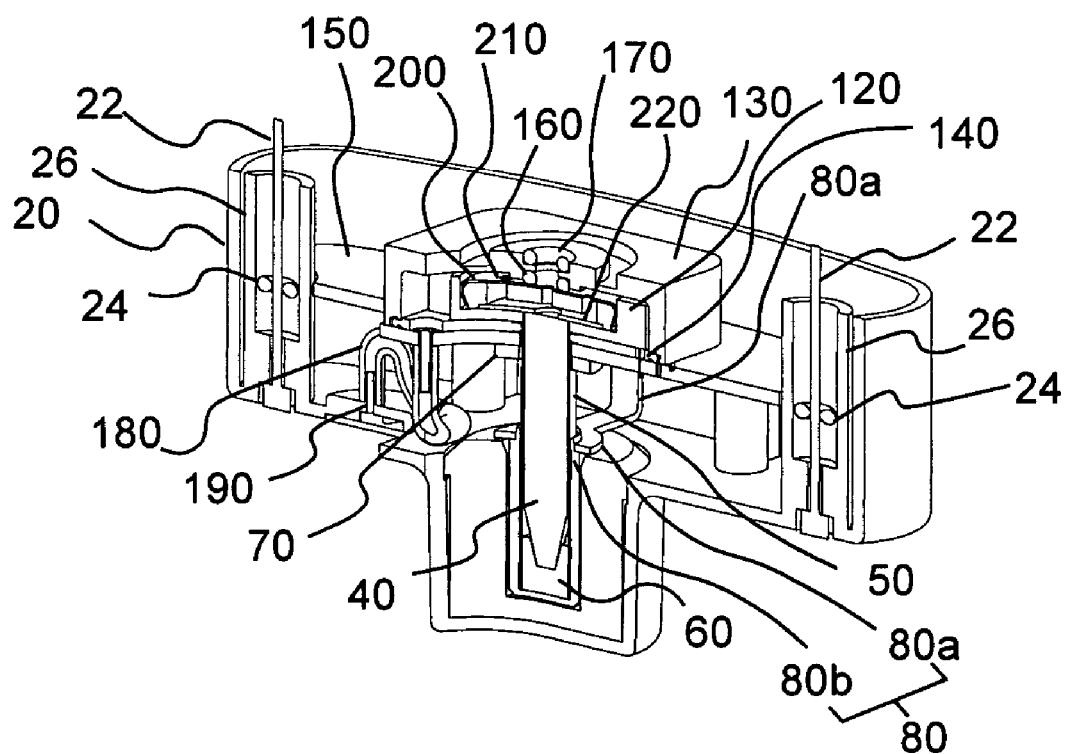
FIG. 2B illustrates a cutaway, perspective view of the PID of FIG. 1 in an assembled state, other than the top enclosure or cap.

FIGS. 1 through 2B illustrate an embodiment of a PID 10 of the present invention, which can, in one embodiment include a detector housing 20 and a cooperating top enclosure or cap 30. Cap 30 can, for example, be maintained in connection with housing 20 via connectors such a screws 22. In the embodiment of FIGS. 1 through 2B, guides 24 (for example, annular members) guide screws 22 through a generally cylindrical screw well 26 to connect to cap 30.

Figure 3A:
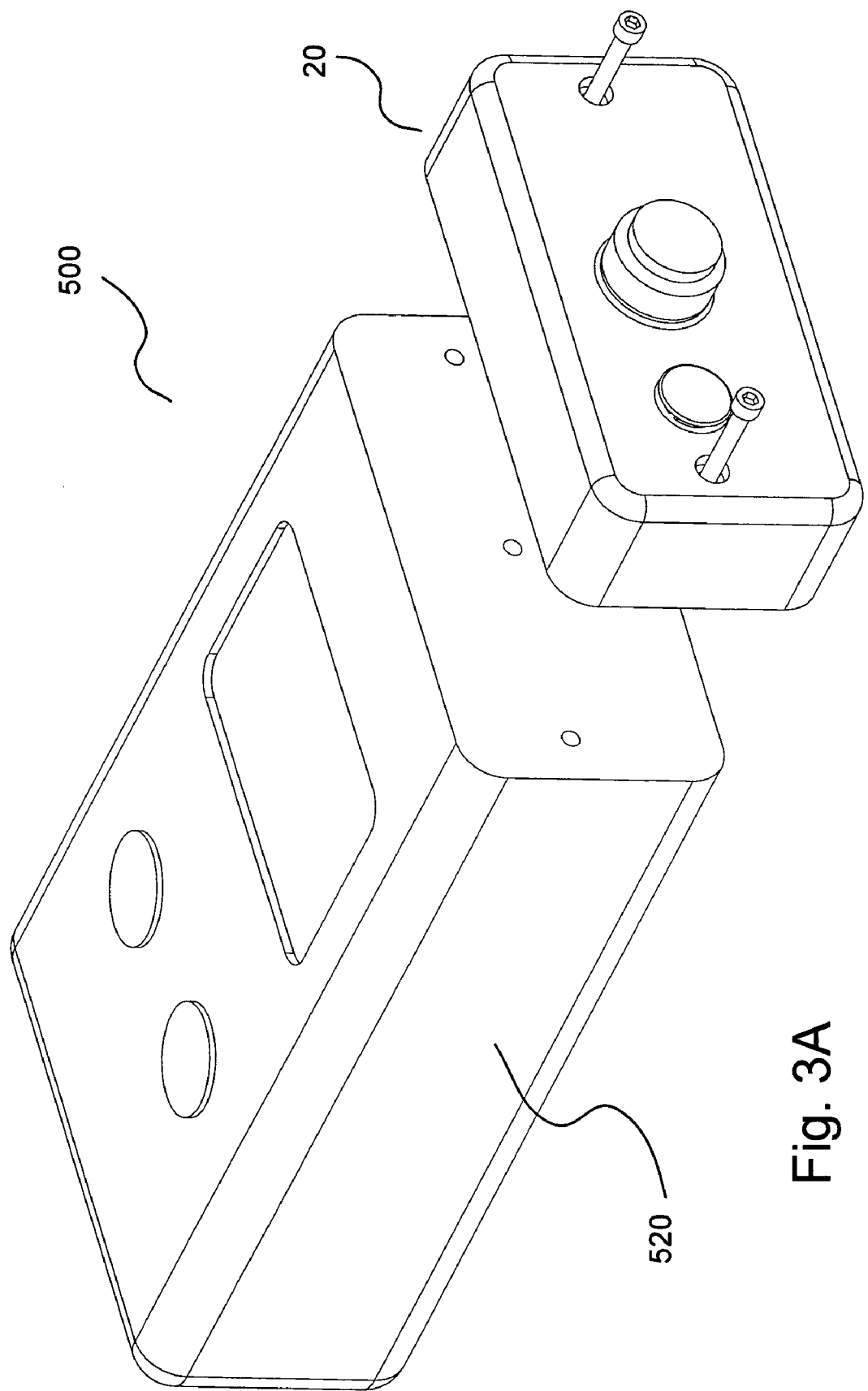
FIG. 3A illustrates a perspective, partially exploded view of the PID of FIG. 1 in attachment to another instrument housing.
Figure 3B:
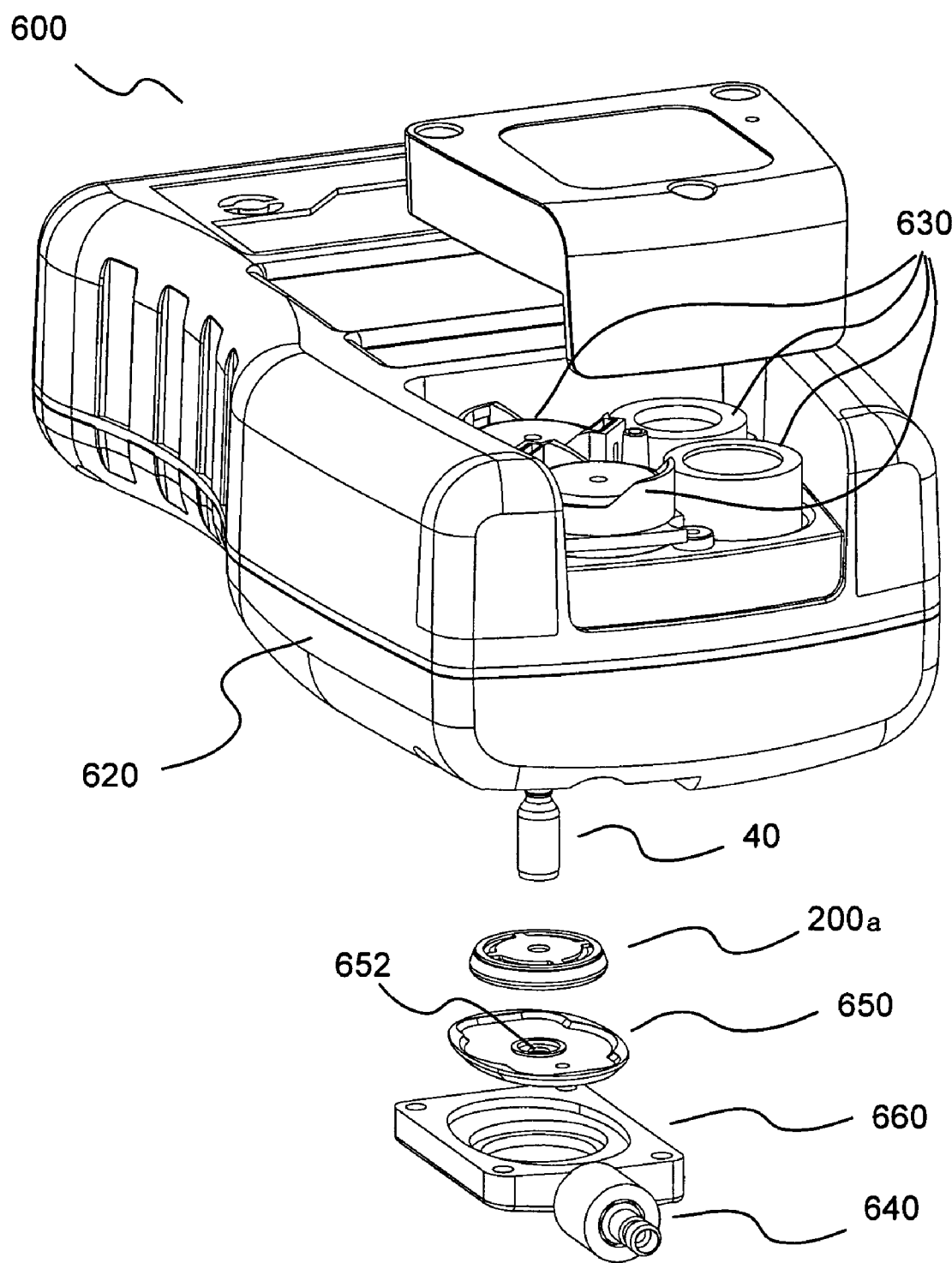
FIG. 3B illustrates a perspective, partially exploded view of selected components of the PID of FIG. 1 as they may be incorporated within the housing of a multi-sensor instrument assembly.

As shown in FIG. 3A, housing 20 can also be connected to another housing 520 of an instrument 500, which can, for example, include one or more other gas sensors. Such other sensors can, for example, be electrochemical gas sensors. An embodiment of an ionization chamber 200a for use in a multi-sensor instrument is shown, for example, in more detail in FIGS. 5A–5D. As shown in FIG. 3B, the components of PID 10 can alternatively be incorporated within the housing 620 of a multi-sensor instrument assembly 600. In either case, some or all of the other gas sensors 630 may be supplied with the same sample of analyte gas as the PID sensor which is described in further detail below, for example, by diffusion or via flow forced by a pump (not shown in FIG. 3B) through a connection fitting 640. In FIG. 3B, vacuum ultraviolet radiation (VUV) lamp 40 and the photoionization chamber assembly 200a (see FIG. 5) of a type viable for use in PID 10 are separately removable from the instrument housing for service or replacement by removing an internal cover piece 650 and an external cover piece 660. A filter for airborne particulates and droplets (not shown) can be positioned in the path of the sample gas before it enters the ionization chamber. Furthermore, the present inventors have discovered that the sensitivity of the PID to humidity in the air can be reduced by causing a pressure differential/drop across the inlet to the ionization chamber. Such a pressure drop results in a decrease in relative humidity. Preferably, the pressure drop is sufficient to cause at least a 5% drop in relative humidity. More preferably, the pressure drop is sufficient to cause at least a 10% drop in relative humidity. Such a pressure drop and the associated drop in relative humidity can be accomplished by positioning one or more restrictive orifices in the gas flow path into the ionization chamber, so that a pressure differential is developed across the orifice(s). Such an orifice 652 can be provided, for example, in the internal cover piece 650 as illustrated in FIG. 3B. Alternatively, for example, a filter with a relatively small pore diameter/size can be used (thereby providing a plurality of orifices of restricted diameter) to create a pressure drop across the inlet to the photoionization chamber.

In the embodiment of FIGS. 1 through 2B, a VUV lamp 40 is slidably and removably disposed within an insulating lamp sleeve 50 and rests at its bottom end upon a lamp pad, seating or spring 60. For example, spring 60 can be a piece of semi-soft tubing which captures and axially centers lamp 40 at its bottom end 40a, and may simultaneously make a gas-flow seal between the lamp envelope and the insulating sleeve 50. In the embodiment shown in FIG. 2C, cap 60b attaches by a screw thread (not shown) to housing section 20a, and is removable by the user to provide easy access to removable lamp 40. An external or internal shoulder 60c can be provided on cap 60b, in order to fix the required depth of insertion of cap 60b into housing 20 and thereby provide the required compressive force on lamp seating or spring 60a of FIG. 2C. In the embodiments shown in FIGS. 1 through 2C, lamp sleeve 50 can be sealed against lamp electrode 70 or base 150 using a sealing compound. In another embodiment, the gasket pad 140 can be configured to project radially into passage 100 to seal against lamp sleeve 50 or the envelope of lamp 40.

The VUV lamp 40 can be of a type which operates with electrodes inside the lamp envelope, or of a type which operates without internal electrodes. In the preferred embodiment shown, a low-pressure gas discharge is induced within VUV lamp 40 by applying appropriate voltage levels to external electrodes 70 and 80, as known in the art. In the embodiment of FIGS. 1 through 2B, electrode 70 is a disk-shaped electrode and electrode 80 is a composite electrode including electrode sections 80a and 80b. When assembled, electrode section 80b attaches into the opening of electrode section 80a to form a single, cup-shaped electrode 80, as shown, for example, in FIG. 2B. AC power can, for example, be transmitted to VUV lamp 40 via rear electrode 80 or via forward electrode 70. FIG. 2C illustrates an alternative embodiment in which electrode 80' is formed as a sleeve. PID 10 can, for example, include a power supply, such as a DC battery which is in connection with a DC to AC converter as known in the art.

Photons generated within VUV lamp 40 are transmitted through a VUV window 90 (at the top of lamp 40 in the orientation shown in FIGS. 1 through 2C). Window 90 can be fabricated from a VUV transmissive crystalline material such as, but not limited to, CaF2, BaF2, MgF2 or LiF. Several established methods are available for affixing a VUV crystal window to a glass tube body to form a low-pressure gas-discharge lamp. These methods include, for example, glass-to-glass seals and adhesive seals.

It is known that electrodeless gas discharge lamps can be more difficult to start at low temperatures or when the gas-filled volume is shielded from any external illumination. Under those conditions it can be more difficult to generate the initial free electrons which will lead to an electrical discharge in the fill gas of the lamp. Several methods are known in the art which will help to enhance the startability of the lamp when its starting voltage is applied. Those methods include heating the lamp; altering the gas fill of the lamp with a plurality of gasses; providing a radioactive source of ionizing particle radiation; and/or providing an electric-field enhancing metal object within or adjacent to the discharge volume.

It is also generally understood that illuminating an additional inner conductive surface region of the discharge volume with externally generated photons of sufficient energy to produce electro-thermal enhanced photo-electron emission from the illuminated surface regions will help to enhance startability of the lamp. The inventors of the present invention have discovered that another method of enhancing startability and operational performance can be provided, for example, by a near-UV or UV light energy source 41 (see FIG. 2C) such as a light-emitting diode (LED). The photons from light energy source 41 are directed through a transparent portion of the envelope of lamp 40, without the use of a conductive surface inside the lamp envelope upon which the photons would impinge. Light energy source 41 can be positioned within housing 20 adjacent to lamp 40, or it can be positioned remote from lamp 40 (and even exterior to housing 20) with the light transmitted to the transparent section of lamp 40 via a light transmitting pathway such as a fiber optic line or a light pipe (not shown in FIG. 2C).

VUV lamp 40 inserts into a passage 100 formed in an ionization chamber enclosure 110, so that its emitted VUV radiation enters a photoionization chamber 200 via an opening 222 formed in the exterior bottom of ionization chamber 200 (in the orientation of FIGS. 1 through 2C), which the lamp window 90 abuts or comes close to. Lamp 40 can be provided with an internal piece of getter material (not shown) to better maintain the purity of the internal gas, as known to those skilled in the art.

Enclosure 110 includes a lower (in the orientation of FIGS. 1 through 2C) seating 120 and an upper cover 130. A sealed connection can be maintained therebetween via, for example, a seal 140 (for example, a gasket). In the embodiment of FIGS. 1 through 2C, seating 120 and gasket 140 are connected to a base 150, for example, a printed circuit board. Analyte gas from the surrounding environment enters ionization chamber 200 via an inlet 132 formed in upper cover 130 of the enclosure 110. Preferably, a seal 160 (for example, an O-ring) forms a sealed passage between inlet 132 and a gas inlet 212 formed in ionization chamber 200. Preferably, another seal 170 (for example, an O-ring) forms a sealed passage between an analyte gas inlet 32 formed in cap 30 and inlet 132. Analyte gas can pass into ionization chamber 200 via sequential inlets 32, 132 and 212 via diffusion or via forced flow (using a pump; see, for example, FIG. 1) as known in the art. Another gas seal is provided by gasket 140 pressing against the lamp sleeve 50. Alternatively, the opening of the lamp sleeve 50 can be sealed against electrode 70 or base 150 using a sealing compound, and the gasket 140 can seal against the body of lamp 40. In the embodiment of FIGS. 1 through 2C, gas exits photoionization chamber 200 via one or more outlets 214a and 214b. Such gas exits PID 10 via exhaust tube 180, which is in fluid connection with an exhaust vent 190.

Unlike most ionization chambers used in currently available PIDs (in which the photoionization chamber is generally integral with the remainder of the PID), ionization chamber 200, including the electrodes therein, is readily removable from PID 10 and replaceable as a unit or a module. Moreover, photoionization chamber 200 and other photoionization chambers of the present invention are relatively simple and inexpensive to manufacture, thereby making it relatively inexpensive to dispose of contaminated photoionization chambers of the present invention and replace those photoionization chambers with new photoionization chambers of the present invention. Further, the photoionization chambers of the present invention are, in many embodiments, easily removable and readily insertable within a PID or other instrument of the present invention, without the need for careful alignment of corresponding electrical contacts and/or mechanical connections. Several embodiments of the photoionization chambers of the present invention are discussed in further detail below in connection with FIGS. 4A through 9.

Referring to FIGS. 4A through 4D, in one embodiment, photoionization chamber 200 includes a first housing member 210 and a second housing member 220. First and second housing members 210 and 220, respectively, can be mechanically connected via, for example, a single mechanical connector such as a gasket ring 230 to create a sealed photoionization chamber 200 having a chamber volume 240.

Inlet 212, by which the analyte molecules and their carrier gas enter into photoionization chamber 200 as described above, is formed in first housing member 210. Once again, the design of inlet port 212 can be chosen as known in the art to allow for diffusive entry of the analyte molecules, or for a metered flow of carrier gas driven by a gas pump on the downstream or upstream side of photoionization chamber 200. One or more exit openings such as outlets 214a and 214b can be formed in, for example, first housing member 210 for a flow or diffusion path by which the analyte molecules and their carrier gas can exit from photoionization chamber 200. Alternatively, the pumped flow of carrier gas can be in the reverse direction, in which case the one or more ports 214a and 214b will be the inlet port(s), and port 212 will be the outlet port. When operated in a diffusion mode, a single port (for example, port 212) can operate as both the inlet port and the outlet port. A microporous filter (not shown) may be used in the path of the carrier gas flowing into the photoionization chamber 200, as known in the art.

In the orientation of FIG. 4B, chamber volume 240 is partly bounded by an upper surface of a cathodic "ion collector" electrode 250 to which positively charged reaction products are attracted. Cathodic electrode 250 can, for example, be formed on or connected to one side of an insulating disk 254. Cathodic collector electrode 250 can be mechanically connected and/or integrated with first housing member 210. Cathodic collector electrode 250 and housing member 210 can also be electrically connected if first housing member 210 is chosen to be conductive. In the embodiment of FIGS. 4A through 4D, cathodic collector electrode 250 and insulating disk 254 typically include a typically central passage 252 through which analyte molecules passing through inlet 212 enter chamber volume 240. A lower surface of an anodic "ion repeller" electrode 260, formed on or connected to an interior surface of second housing member 220, is spaced from the upper surface of cathodic electrode 250 to further define chamber volume 240. In the embodiment of FIGS. 4A through 4D, anodic electrode 260 and second housing member 220 rest on a ledge 232 formed in gasket 230 to space anodic electrode 260 from cathodic electrode 250. In one embodiment, each of cathodic electrode 250 and anodic electrode 260 were fabricated from stainless steel.

First housing member 210 can, for example, be at least partially fabricated from a thin non-magnetic stainless steel for the purposes of electrical connection and electromagnetic shielding. The assembly of first housing member 210 and second housing member 220 is similar to the assembly of the "button cell" electrochemical sensors described in U.S. Pat. No. 5,667,653, assigned to the assignee of the present invention, the disclosure of which is incorporated herein by reference. For example, after assembly of the parts thereof, a rim 216 of first housing member 210 can be pressed radially inward or crimped against a single mechanical connector such as gasket 230 to create a leak-proof mechanical seal therebetween. Connector or gasket 230 can be fabricated from an insulating material to provide electrical insulation between first housing member 210 and second housing member 220. The fabrication technique of the present invention is less complicated, faster and less expensive than prior fabrication techniques for photoionization chambers.

An electrical connection from the cathodic electrode 250 to first housing member 210 can be provided. This connection can, for example, be accomplished by plating passage 252 or by providing one or more other conductive paths through the thickness of insulating disk 254. Alternatively, disk 254 can be entirely conductive, in which case it serves as the cathodic electrode, and a distinct electrode element 250 is not needed on its surface. Likewise, an electrical connection from anodic electrode 260 to the external surface of second housing member 220 can be provided. This connection can, for example, be accomplished by providing one or more conductive paths through the thickness of an insulating second housing member 220 to connect to one or more conductive areas on the opposing side of second housing member 220. Second housing member 220 can alternatively be made entirely conductive, in which case it serves as the anodic electrode, and a distinct electrode element 260 is not needed on its surface.

In one embodiment, first housing member 210 and disk 254 are conductive and electrically connected, and first housing member 210 forms an electrical connection with one or more electrical connections 192 of seating 120 (see FIG. 1). In a further embodiment, second housing member 220 is conductive and serves as the anodic electrode. In this embodiment, second housing member 220 forms an electrical connection with one or more other electrical connections 194 of seating 120 in a manner similar to a battery in a battery holder. Cover 130 can be metal that is grounded to form an electrical shield. Second housing member 220 can be conductive over at least a part of its external surface for the purpose of electrical connection.

In several embodiments, the conductive portions of each of first housing member 210 and second housing member 220 (and other housing members of the photoionization chambers of the present invention), which can be the entirety thereof, extend annularly (although not necessarily symmetrically) around axis A so that no specific rotational alignment of photoionization chamber 200 about axis A is required to form electrical contacts within, for example, PID 10 as described above. Moreover, as the surface of the housing members can act as electrical contacts in several embodiments of the photoionization chambers of the present invention, there is no requirement for alignment in any orientation or plane of extending electrical contacts such as pins.

As described above in connection with PID sensor 10, VUV radiation from gas discharge lamp 40 enters photoionization chamber 200 through opening or inlet 222 in second housing member 220. In one embodiment, lamp 40 is an electrodeless sealed glass tube filled with a particular low-pressure discharge gas or gas mixture as known in the art. One portion or end of the glass lamp tube is sealed with a VUV-transmissive crystalline section or window 90 which can abut second housing member 220 over, for example, a generally circular area around inlet 222. Although second housing member 220 can be made entirely conductive, it can be advantageous to form at least the portion thereof contacted by window 90 from a material with a very low quantum efficiency for production of photoelectrons (see, for example, FIGS. 7A through 7D discussed below).

It can also be beneficial to coat at least the cathodic electrode 250 on its ion-collecting side with a thin (for example several tens of microns) and generally uniform layer 256 of substantially VUV-absorptive material, such as polytetrafluoroethylene (PTFE), to suppress the production and/or emission of photoelectrons from cathodic electrode 250 as a result of the VUV radiation from lamp 40. Cathodic electrodes on some currently available PIDs (for example U.S. Pat. No. 5,773,833) are thin and perforated for the through-diffusion of analyte ions, with the VUV-absorbing coating only on the side thereof facing the VUV lamp. However, the inventors of the present invention have discovered that a thin layer 256 on the ion-collecting side of cathodic electrode 250 of the present invention performed the VUV-blocking function, while still allowing the detection of positively charged reaction products by their impingement onto and/or through layer 256 on cathodic electrode 250. Anodic electrode 260 can also be provided with a similarly thin layer 266 of an insulating material, which may also be substantially VUV-absorptive. Insulating layers 256 and/or 266 can be extended along the underlying surfaces to assist in preventing current leakage between electrodes 250 and 260. These electrode coating layers can also be slightly conductive. Allowing for a slightly conductive electrode layer will affect the amount of current leakage. The coatings can, for example, be made of PTFE which contains carbon particles, or any other similar construction.

The PIDs of the present invention can optionally be supplied with bare metal for the cathode and/or anode surfaces which face the electrode gap. Even in the case of uncoated electrode surfaces, the quantum efficiency for VUV production of photoelectrons is mitigated somewhat by the thin metal oxide film which naturally forms on metal surfaces which have been exposed to air. The formation of this beneficial metal oxide film can preferably be expedited by heating the metal electrode parts in air at a high temperature for up to several hours.

PID 10 further includes circuitry as known in the art to: (a) provide independent steady or varying voltages to cathodic electrode 250 and to anodic electrode 260 of ionization photoionization chamber 200; (b) measure an output signal at the level of, for example, picoamperes resulting from impact of positive ions on cathodic electrode 250 during operation of PID 10; and (c) provide independent steady or varying voltages to the electrodes of gas discharge lamp 40. Lamp 40 is typically driven at a sinusoidal frequency in the kilohertz to megahertz range, as known in the art. In one method, the amplitude of the sinusoidal lamp voltage can be modulated to reduce the average power to the lamp, as known in the art (see for example U.S. Pat. No. 5,773,833).

The ionization chambers of the present invention can also be used with alternative means of producing the necessary ionization of analyte molecules within chamber volume 240. Examples of such other means include multi-step ionization by one or more laser beams, injection of metastable excited gas species and/or VUV photons from a discharge or spark chamber into ionization chamber 200 (see for example U.S. Pat. Nos. 5,541,519 and 6,333,632), low activity radioactive sources of ionizing particles (see for example U.S. Pat. No. 4,704,336), or electrical field ionization of the analyte molecules by applying brief high-voltage pulses via electrodes 250 and 260. Other means of producing ionization can be recognized by those skilled in the art.

As set forth above, readily removable (and easily reinsertable) photoionization chamber 200 of the present invention enables quick and inexpensive remedying/repair of PID 10 in which photoionization chamber 200 has become contaminated, by simple replacement of photoionization chamber 200. Moreover, the removable and replaceable nature of the photoionization chambers of the present invention allow PID 10 to be adjusted for different environmental or ambient conditions as well as certain manners of use of PID 10 by incorporating therein a photoionization chamber selected for those conditions or manners of use. In that regard, several alternative embodiments of photoionization chambers are set forth in FIGS. 5A through 9.

Photoionization chamber 200a of FIGS. 5A through 5D is generally similar in design and operation to photoionization chamber 200. Like components of photoionization chamber 200a are numbered similarly to corresponding components of photoionization chamber 200, with the addition of the designation "a". In comparison to second housing member 220 and anodic electrode 260 of photoionization chamber 200, however, the surface area of second housing member 220a and thereby the surface area of second electrode 260a of photoionization chamber 200a are reduced. In that regard, the diameter of most of second housing member 220a and the diameter of anodic electrode 260a are reduced. Second housing member 220a is connected to gasket 230a via a plurality of (that is, two or more) radially outward extending flanges or tabs 224a. The inventors of the present invention have discovered that photoionization chamber 200a can provide improved performance as compared to photoionization chamber 200 for ambient environments and/or carrier gas flows having high humidity. It is believed that the reduced surface area of anodic electrode 260a results in less current leakage between the electrodes in high-humidity environments. Also, in some embodiments of PID 10, the additional gas flow paths provided by the open areas between the tabs 224a render ports 214aa and 214ab in housing member 210a unnecessary, in which case said ports need not be present.

Another embodiment of a photoionization chamber 300 of the present invention, as illustrated in FIGS. 6A through 6D, includes a first housing member 310 and second housing member 320. First and second housing members 310 and 320, respectively, are mechanically connected via, for example, a mechanical connector such as a gasket ring 330 via crimping of rim 316 of first housing member 310 to create photoionization chamber 300 having a chamber volume 340.

Analyte molecules and their carrier gas enter into photoionization chamber 300 via inlet 312 as described above. One or more exit openings or outlets 314a and 314b provide a flow or diffusion path by which the analyte molecules and their carrier gas can exit from photoionization chamber 300. Chamber volume 340 is partly bounded by an upper or inner surface of a cathodic electrode 350, which can be formed on or connected to one side of an insulating disk 354. Cathodic collector electrode 350 and insulating disk 354 include a typically central passage 352 through which analyte molecules passing through inlet 312 enter chamber volume 340.

In the orientation of FIG. 6B, a lower surface of an anodic electrode 360 is spaced from the upper surface of cathodic electrode 350 to further define chamber volume 340. The surfaces of cathodic electrode 350 and/or anodic electrode 360 which face the volume 340 can be coated with thin layers 356 and 366, respectively, of insulating (or partially conductive) and/or VUV-absorptive material as described above.

In the embodiment of FIGS. 6A through 6D, cathodic electrode 350 is spaced from anodic electrode 360 via an annular spacer 370. Adjustment of the height of spacer 370 adjusts the distance between cathodic electrode 350 and anodic electrode 360, thereby changing the response of PID 10. Moreover, spacer 370 can provide improved resistance to physical shocks or impact forces for photoionization chamber 300 as compared to other photoionization chambers. Improved resistance to physical shocks or impact forces can be particularly beneficial in the case of portable or handheld detectors Another embodiment of a photoionization chamber 400 of the present invention, as illustrated in FIGS. 7A through 7D, includes a first housing member 410 and second housing member 420. Similar to photoionization chambers 200, 200a and 300, first and second housing members 410 and 420, respectively, are mechanically connected via, for example, a mechanical connector such as a gasket ring 430 via crimping of rim 416 of first housing member 410 to create photoionization chamber 400 having a chamber volume 440.

Also similar to photoionization chambers 200, 200a and 300, analyte molecules and their carrier gas enter into photoionization chamber 400 via inlet 412 as described above. One or more exit openings or outlets 414a and 414b provide a flow or diffusion path by which the analyte molecules and their carrier gas can exit from photoionization chamber 400.

Chamber volume 440 is partly bounded by an upper or inner surface of a cathodic electrode 450, which can be formed on or connected to the upper or inner side of an insulating disk 454 (for, example, fabricated from circuit board). In the embodiment of FIGS. 7A through 7D the diameter of cathodic electrode 450 is less than the diameter of disk 454. In the orientation shown, a lower side of disk 454 is attached to the interior surface of first housing member 410. An electrical connection can be provided between cathodic electrode 450 and first housing member 410 through insulating disk 454 as described above. Cathodic collector electrode 450 and disk 454 include a generally central passage 452 through which analyte molecules passing through inlet 412 enter chamber volume 440. Disk 454 also includes passages 456 and 458 for fluid communication with passages 414a and 414b, respectively, of first housing member 410.

In the orientation shown in FIG. 7B, a lower surface of an anodic electrode 460 is spaced from the upper surface of cathodic electrode 450 to further define chamber volume 440. The surfaces of cathodic electrode 450 and/or anodic electrode 460 which face the volume 440 can be coated with thin layers of insulating (or partially conductive) and/or VUV-absorptive material (not shown) as described above. In this orientation, anodic electrode 460 is attached to or formed on a lower surface of second housing member 420. In the embodiments of FIGS. 7A through 7D, second housing member 420 includes generally annular insulating sections 425 and 427 and an intermediate, generally annular conductive section 428. Electrical connection can be provided between conductive section 428 and anodic electrode 460. As described above, the portion of the VUV radiation that leaves the VUV lamp and impinges on insulating section 427, formed around inlet 422, will not produce photoelectrons, which can result in noise and interference in the very small signal of the ion current.

Figure 8:
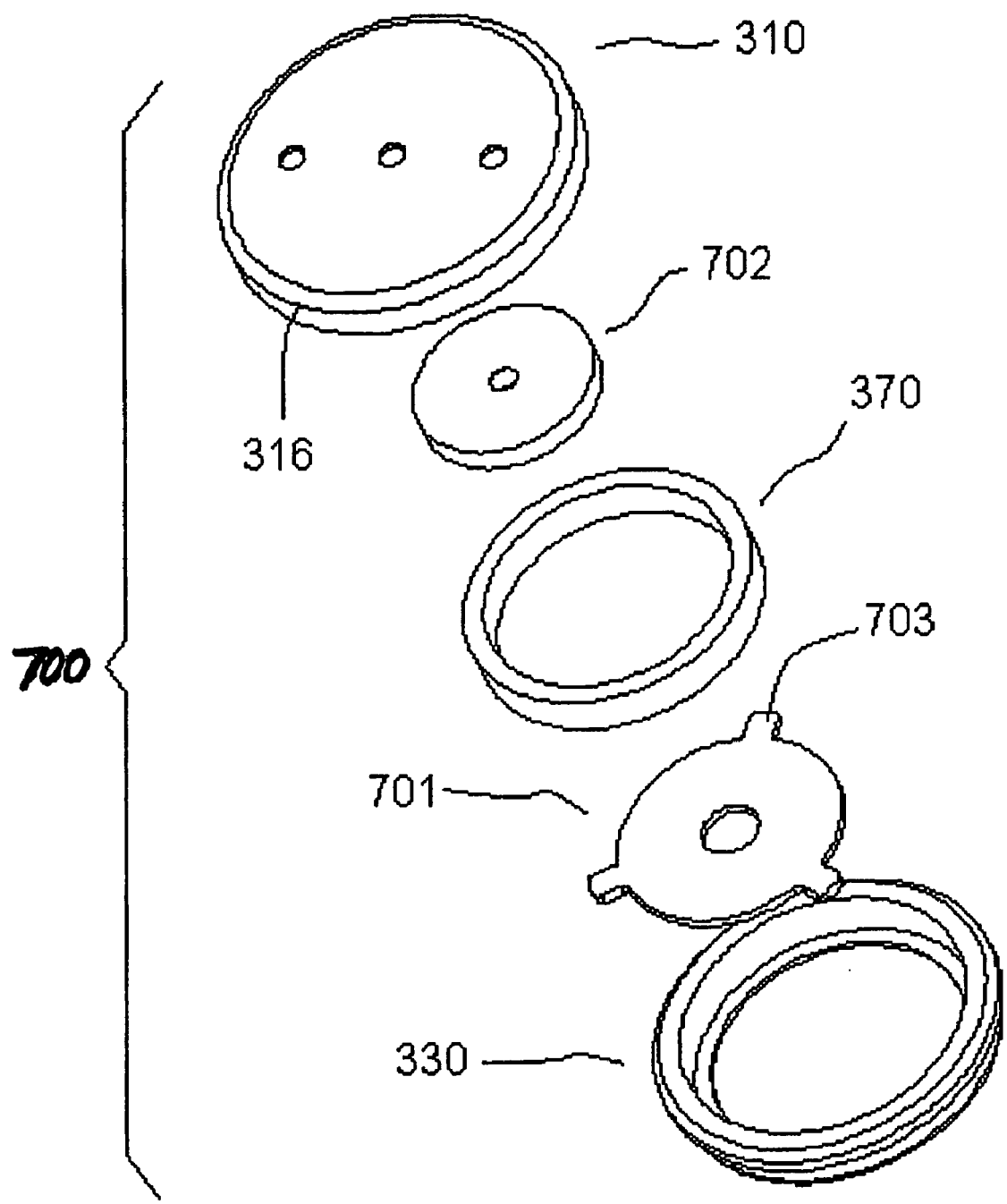
FIG. 8 illustrates a perspective, exploded view of another embodiment of an ionization chamber of the present invention.

Another embodiment of a photoionization chamber 700 of the present invention is illustrated in FIG. 8. It combines the beneficial mechanical stability of the chamber gaskets 330 and 370, illustrated in FIGS. 6A–6D, with second housing member 701 which has a plurality of peripheral tabs 703 for good dielectric performance and reduced sensitivity to humidity (similar to the design of second housing member 220a which is shown in FIGS. 5A–5D). Chamber 700 includes a first housing member 310, to which is connected a cathodic collector electrode 702. In one preferred embodiment, housing member 310 and cathodic electrode element 702 are made from non-magnetic metal and mechanically and electrically joined, for example by spot-welding. First and second housing members 310 and 701, respectively, are mechanically connected via, for example, a mechanical connector such as a gasket ring 330 via crimping of rim 316 of first housing member as described above. Any or all of the surfaces of housing member 310, electrode element 702 and second housing member 701 which are exposed to the inner chamber volume or which seal against gasket 330 or 370 can be coated with a thin layer of insulating and/or VUV-absorptive material, as described above.

Figure 9:
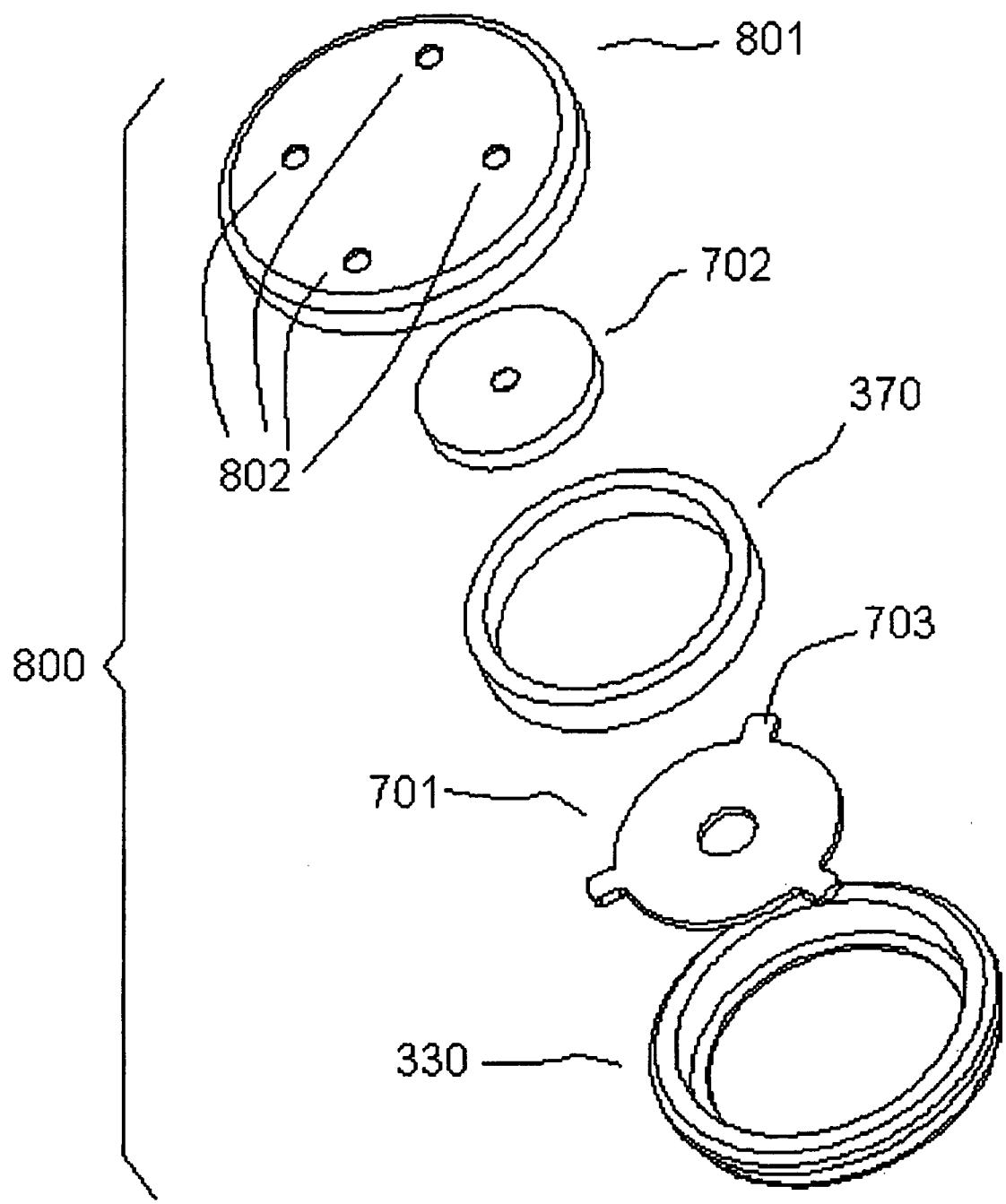
FIG. 9 illustrates a perspective, exploded view of another embodiment of an ionization chamber of the present invention, which allows for an alternative gas flow path.

Another embodiment of a photoionization chamber 800 of the present invention is illustrated in FIG. 9. It is identical to photoionization chamber 700 shown in FIG. 8, except for the design of the first housing member 801. In this case, the central portion of housing member 801 is closed, and there is now a pattern of openings 802 (one or more) which open into the peripheral region of the ion chamber's internal open volume. In this embodiment, the O-ring 160 shown in FIG. 1 is not present, so that the sampled gas is free to flow via inlet 132 directly into the full volume of enclosure 110. As the gas flow exits the enclosure 110 via exit tube 180, it is free to flow and diffuse through ion chamber 800 via openings 802 and the open spaces between second housing member 701 and gasket ring 330.

The foregoing description and accompanying drawings set forth preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A photoionization detector comprising:
   a housing;
   electrical contacts within the housing;
   a photoionization chamber within the housing, the photoionization chamber including a cathodic electrode and an anodic electrode, the photoionization chamber and the associated cathodic electrode and anodic electrode being removable from within the housing as a unit, the photoionization chamber making electrical connection with the electrical contacts when seated in the housing regardless of the rotational orientation of the photoionization chamber about an axis; and
   a lamp to transmit VUV photons to within the photoionization chamber.

2. The photoionization detector of claim 1 wherein a side of the cathodic electrode which attracts positively charged reaction products is coated with a layer of material that allows the electrical detection of at least a portion of the positively charged reaction products impinging upon the layer.

3. The photoionization detector of claim 2 wherein the layer of material on the cathodic electrode is also VUV absorptive.

4. The photoionization detector of claim 1 wherein a side of the anodic electrode which repels positively charged reaction products is coated with a layer of material that allows the collection of at least a portion of the negatively charged reaction products impinging upon the layer.

5. The photoionization detector of claim 4 wherein the layer of material on the anodic electrode is also VUV absorptive.

6. The photoionization detector of claim 2 wherein the layer of material on the cathodic electrode is of generally uniform thickness over the coated area of the cathodic electrode.

7. The photoionization detector of claim 4 wherein the layer of material on the anodic electrode is of generally uniform thickness over the coated area of the anodic electrode.

8. The photoionization detector of claim 1 wherein the photoionization chamber includes a cathodic chamber housing member in electrical connection with the cathodic electrode, at least a portion of the surface of the cathodic chamber housing member forming an electrical contact.

9. The photoionization detector of claim 1 wherein the photoionization chamber includes an anodic chamber housing member in electrical connection with the anodic electrode, at least a portion of the surface of the anodic chamber housing member forming an electrical contact.

10. The photoionization detector of claim 8 wherein the cathodic chamber housing member is formed entirely from a conductive metal.

11. The photoionization detector of claim 9 wherein the anodic chamber housing member is formed entirely from a conductive metal.

12. The photoionization detector of claim 1 wherein the photoionization chamber comprises:
a first chamber housing member in electrical connection with the cathodic electrode, at least a portion of the surface of the first chamber housing member forming a first electrical contact;
a second chamber housing member in electrical connection with the anodic electrode, at least a portion of the surface of the second chamber housing member forming a second electrical contact;
wherein the first chamber housing member and the second chamber housing member are each formed entirely from a conductive metal and are mechanically connected to an insulating connector.

13. The photoionization detector of claim 12 wherein the photoionization chamber includes a plurality of openings which are distributed among the first chamber housing member and the second chamber housing member, and through which a sample gas may pass.

14. The photoionization detector of claim 12 wherein the insulating connector is annular in shape.

15. The photoionization detector of claim 14 wherein the first chamber housing member and the second chamber housing member are mechanically connected to the annular, insulating connector via crimping.

16. A photoionization device for use with a forced flow of sample gas, comprising:
a housing;
a photoionization chamber within the housing;
a VUV lamp to transmit VUV photons to a photoionization volume within the photoionization chamber;
an orifice upstream of the photoionization volume such that the pressure in the photoionization reaction volume is less than the pressure on the other side of the orifice
thereby reducing the relative humidity of the sample gas within the photoionization volume compared to the relative humidity of the sample gas before entering the photoionization device.

17. The photoionization device of claim 16 wherein a plurality of orifices are placed upstream of the photoionization volume.

18. The photoionization device of claim 16 wherein the reduction in relative humidity is at least 5%.

19. A photoionization detector comprising:
a housing;
a photoionization chamber within the housing;
a VUV lamp to transmit VUV photons to within the photoionization chamber;
and at least one source of photons outside the VUV lamp which can be electrically activated to illuminate an inner surface of the VUV lamp in order to enhance the startability and operational performance of said VUV lamp.

20. The photoionization detector of claim 19 wherein the source of photons outside the VUV lamp is a light emitting diode.

* * * * *